United States Patent
Chu et al.

(10) Patent No.: US 6,894,159 B2
(45) Date of Patent: *May 17, 2005

(54) PROCESS FOR THE PREPARATION OF 2'-FLUORO-5-METHYL-BETA-L-ARABINO-FURANOSYLURIDINE

(75) Inventors: Chung K. Chu, Athens, GA (US); Jinfa Du, Irvine, CA (US); Yongseok Choi, Athens, GA (US)

(73) Assignee: The University of Georgia Research Foundation, Athens, GA (US)

( * ) Notice: Subject to any disclaimer, the term of this patent is extended or adjusted under 35 U.S.C. 154(b) by 120 days.

This patent is subject to a terminal disclaimer.

(21) Appl. No.: 10/351,222

(22) Filed: Jan. 24, 2003

(65) Prior Publication Data

US 2003/0139593 A1 Jul. 24, 2003

Related U.S. Application Data

(63) Continuation of application No. 09/121,294, filed on Jul. 23, 1998, now Pat. No. 6,512,107.
(60) Provisional application No. 60/053,488, filed on Jul. 23, 1997.

(51) Int. Cl.$^7$ .................... C07H 19/00; C07H 19/22
(52) U.S. Cl. ........... 536/27.4; 536/28.5; 536/28.51; 536/28.52; 536/28.53; 536/28.54; 536/28.1; 536/25.3; 536/28.31
(58) Field of Search ............... 536/27.4, 28.5, 536/28.51, 28.52, 28.53, 28.54, 28.1, 25.3, 25.31

(56) References Cited

U.S. PATENT DOCUMENTS

| | | |
|---|---|---|
| 5,565,438 A | 10/1996 | Chu et al. |
| 5,567,688 A | 10/1996 | Chu et al. |
| 5,587,362 A | 12/1996 | Chu et al. |
| 5,808,040 A | 9/1998 | Chu et al. |
| 6,512,107 B2 * | 1/2003 | Chu et al. .............. 536/27.4 |

FOREIGN PATENT DOCUMENTS

| | | |
|---|---|---|
| CS | 149472 B | 7/1973 |
| CS | 275890 | 3/1992 |
| EP | 1327637 A1 | 7/2003 |
| WO | WO 89/07602 | 8/1989 |
| WO | WO 95/20595 A1 | 8/1995 |
| WO | WO 99/05157 A1 | 2/1999 |
| WO | WO 99/05158 A1 | 2/1999 |

OTHER PUBLICATIONS

Abe, Y., et al., "Epimerization of Aldoss Catalyzed By Dioxobis (2,4–Pentanedionato–O,O')Molybdenum(VI). An Improved Procedure for C–2 Epimer Preparation," *Chem. Pharm. Bull.*, 28(4):1324–1326 (1980). Provided as *Chem. Abs.* AN 1980:495507 (DN 93:95507).

Bilik, V., et al., "Reactions of Saccharides Catalyzed by Molybdate Ions. VII. Preparation of L–Ribose, D–and L–Lyxose," *Chem. Zvesti*, 27(4):547–550 (1973). Provided as *Chem. Abs.* AN 1974:83428 (DN 80:83428).

Greene et al., *Protective Groups in Organic Synthesis*, 2nd ed., John Wiley, 1991.

Jung, M., et al., "Efficient Synthesis of L–Ribose and 2–Deoxy L–Ribose from D–Ribose and L–Arabinose," *Tetrahedron Lett.*, (Elsevier Science Publishers), 38(24):4199–4202 (1997).

Lin, T.–S., et al., "Synthesis of Several Pyrimidine L–Nucleoside Analogues as Potential Antiviral Agents," *Tetrahedron*, 51(4):1055–1068 (Jan. 23, 1995).

Visser, G.M., et al., "Synthesis of the Mirror Image of the RNA Fragment D–CAAGG: a Model Compound to Study Interactions Between Oligonucleotides of Opposite Handedness," *Recl. Trav. Chim. Pays–Bas*, 105(12):528–537 (1986). Provided as *Chem. Abs.* AN 1987:497057 (DN 107:97057).

* cited by examiner

*Primary Examiner*—James O. Wilson
*Assistant Examiner*—Howard V. Owens
(74) *Attorney, Agent, or Firm*—Sherry M. Knowles, Esq.; King & Spalding, LLP

(57) ABSTRACT

The present invention relates to a novel and improved process for preparing 2'-fluoro-5-methyl-β-L-arabinofuranosyluridine represented by formula (1) which shows anti-viral activity, especially potent anti-viral activity against hepatitis B-virus and Epstein-Barr virus:

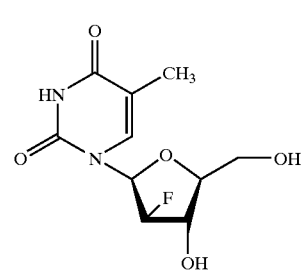

(1)

12 Claims, 1 Drawing Sheet

PROCESS FOR THE PREPARATION OF 2'-FLUORO-5-METHYL-BETA-L-ARABINO-FURANOSYLURIDINE

This application claims priority to U.S. provisional application Ser. No. 60/053,488, filed on Jul. 23, 1997, and also a continuation to U.S. application Ser. No. 09/121,294 filed on Jul. 23, 1998 now Pat. No. 6,512,107.

The present invention relates to an improved process for preparing 2'-fluoro-5-methyl-β-L-arabinofuranosyluridine (generic name: Levovir, hereinafter referred to as "L-FMAU") represented by formula (1), which shows anti-viral activity, especially potent anti-viral activity against hepatitis B-virus (HBV) and Epstein-Barr virus (EBV).

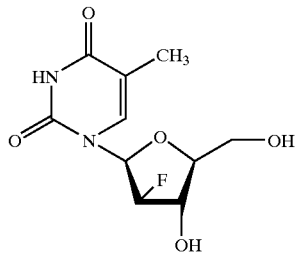

(1)

BACKGROUND OF THE INVENTION

International Publication No. WO 95/20595, and U.S. Pat. Nos. 5,587,362; 5,567,688; and 5,565,438 disclose L-FMAU and derivatives of formula (2):

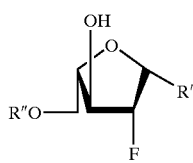

(2)

in which R' represents purine or pyrimidine base; and

R" represents hydrogen, acyl, alkyl, monophosphate, diphosphate or triphosphate.

Nucleoside compounds of formula (2) exhibit anti-viral activity against HBV and EBV. Among these nucleoside compounds, L-FMAU shows particularly potent anti-viral activity against HBV and EBV with very low cytotoxicity and is, therefore, preferred as an anti-viral agent. Nucleoside compounds of formula (2), including L-FMAU, are useful in the prevention and treatment of HBV infections and related conditions, such as anti-HBV antibody positive and HBV-positive conditions, chronic liver inflammation caused by HBV, cirrhosis, acute hepatitis, fulminant hepatitis, chronic persistent hepatitis, and fatigue. In addition, they can also be used for the treatment of EBV-associated disorders.

According to the method disclosed in International Publication No. WO 95/20595, L-FMAU of formula (1) may be prepared using L-xylose of formula (3) as a starting material:

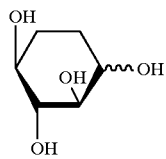

(3)

L-xylose of formula (3) cannot be obtained from natural substances and must therefore be produced by synthetic methods. When L-xylose is used as the starting material, the production cost of L-FMAU is therefore very high.

It has now been discovered that L-FMAU can be economically prepared from L-arabinose, which is present in many natural substances and, thus, is an inexpensive starting material, thereby completing the present invention.

SUMMARY OF THE INVENTION

An improved process for preparing L-FMAU is provided which uses L-arabinose as the starting material.

BRIEF DESCRIPTION OF THE INVENTION

Figure 1:
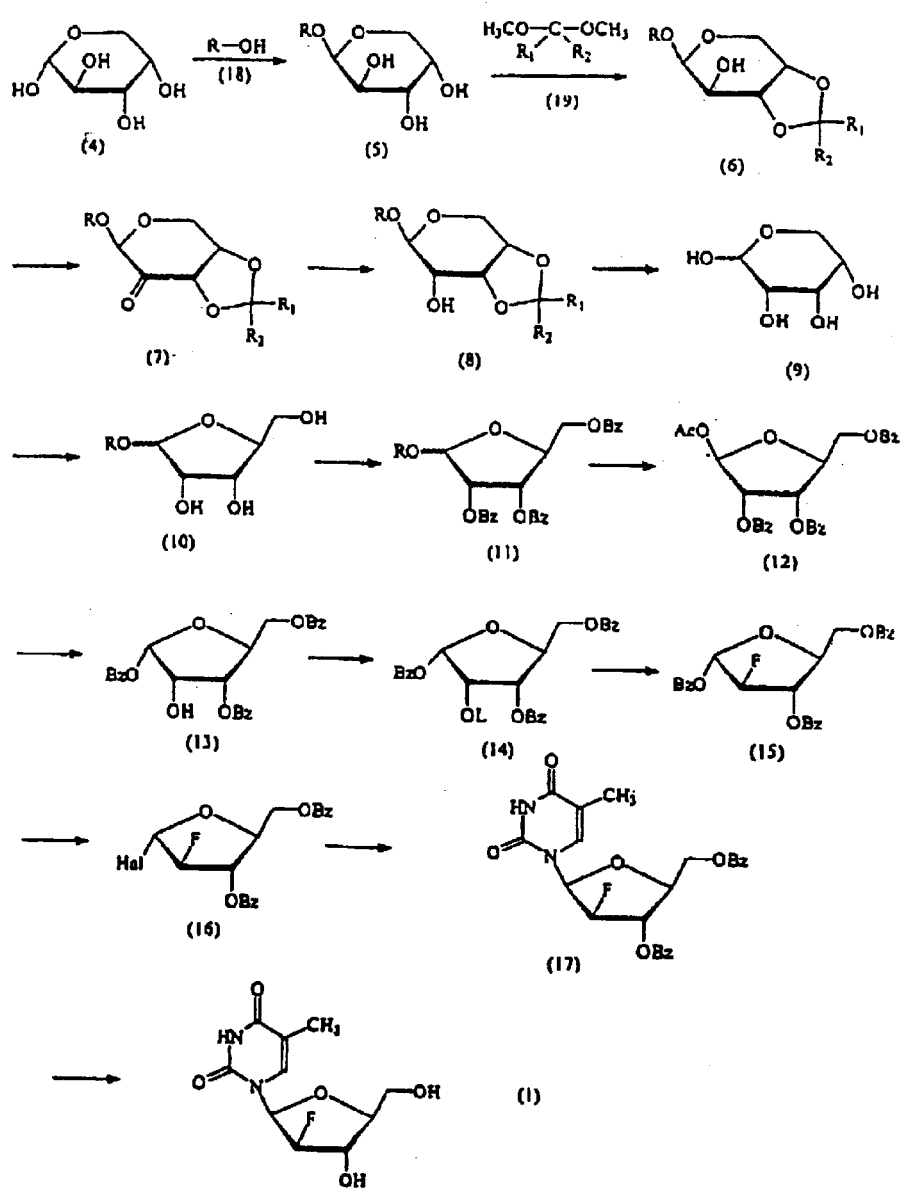
FIG. 1 is a schematic diagram of one method for the production of L-FMAU according to the disclosed process.

The term alkyl, as used herein, unless otherwise specified, refers to a saturated straight, branched, or cyclic, primary, secondary, or tertiary hydrocarbon of $C_1$ to $C_{10}$ and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991. The term lower alkyl, as used herein, and unless otherwise specified, refers to a $C_1$ to $C_4$ saturated straight or branched alkyl group.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term aralkyl or arylalkyl refers to an aryl group with an alkyl substituent.

The term acyl refers to moiety of the formula —C(O)R, wherein R' is alkyl; alkoxyalkyl including methoxymethyl; arylalkyl including benzyl; aryloxyalkyl such as phenoxymethyl; aryl including phenyl optionally substituted with halogen, $C_1$ to $C_4$ alkyl or $C_1$ to $C_4$ alkoxy.

According to the present invention, the desired compound, L-FMAU, of formula (1) can be economically prepared from the starting material of formula (4) by a process that utilizes the reaction set out in FIG. 1, wherein:

a) the starting material, L-arabinose of formula (4), is reacted with a compound of formula (18) to obtain a compound of formula (5);

b) the compound of formula (5) is condensed with a compound of formula (19) to obtain the compound of formula (6), which is oxidized to obtain the compound of formula (7), which is then reduced to obtain the compound of formula (8);

c) the compound of formula (8) is treated with an acid to obtain the compound of formula (9), which is treated with the compound of formula (18) in the presence of an acid to obtain the compound of formula (10), which is reacted with an acyl-chloride such as benzoyl chloride to obtain the compound of formula (11), which is then reacted with an acid, for example, acetic acid and acetic anhydride in the presence of sulfuric acid to obtain the compound of formula (12);

d) the compound of formula (12) is converted into the compound of formula (13);

e) the compound of formula (13) is reacted with an agent for introducing a reactive leaving group to obtain the compound of formula (14);

f) the compound of formula (14) is fluorinated to obtain the compound of formula (15), which is subjected to halogenation to obtain the compound of formula (16), which is then condensed with a thymine base to obtain the compound of formula (17); and g) the compound of formula (17) is treated with ammonia in methanol to produce the desired L-FMAU of formula (1).

In the above reaction scheme, R represents a hydroxy-protecting group such as alkyl, aryl, halogenoalkyl, aralkyl, etc., $R_1$ and $R_2$ independently of one another represent hydrogen, alkyl or aryl, L represents a reactive leaving group such as imidazolyl sulfonyl, toluene sulfonyl, methanesulfonyl, trifluoromethanesulfonyl, etc., and Hal represents a halogen atom such as chloro or bromo.

The process of the present invention is explained in more detail below.

As illustrated in FIG. 1, by reacting the starting material, L-arabinose of formula (4), with an alcohol of formula (18), for example, benzyl alcohol, in the presence of hydrogen chloride gas, the 1-hydroxy group of L-arabinose is protected to produce the compound of formula (5).

In reaction b), the compound of formula (5) prepared in the reaction a) is condensed with a propane derivative of formula (19), for example, 2,2-dimethoxypropane, to produce the compound of formula (6). The compound of formula (6) is oxidized to produce the compound of formula (7), which is subsequently reduced to produce the compound of formula (8). In this reaction, oxidizing agents which can preferably be used include aqueous chromic acid ($CrO_3$), sodium dichromate ($Na_2CrO_7$), pyridinium chlorochromate (POC), pyridinium dichromate (PDC), potassium permanganate ($KMnO_4$), lead tetraacetate/pyridine, oxygen over platinum/carbon catalyst, $RuO_4$, $RuO_4/NaIO_4$, dimethylsulfoxide/dicyclohexylcarbo-diimide (DMSO/DCC) and a proton donor, silver carbonate, triphenyl bismuth carbonate, Oppenauer oxidation (aluminum alkoxides in acetone), chlorine dioxide ($ClO_2$), dimethylsulfoxide/oxalyl chloride (DMSO/$(COCl)_2$), dimethylsulfoxide/sulfuryl chloride (DMSO/$SO_2Cl_2$), dimethylsulfoxide/thionyl chloride (DMSO/$SOCl_2$), dimethylsulfoxide/toluene sulfonyl chloride (DMSO/TsCl), dimethylsulfoxide/trifluoroacetic anhydride (DMSO/$(CF_3CO)_2O$), dimethylsulfoxide/acetic anhydride (DMSO/$Ac_2O$), etc. Among them, pyridinium dichromate in the presence of a solvent such as dichloromethane is particularly preferred. Reducing agents which can preferably be used include sodium borohydride ($NaBH_4$), diisobutyl-aluminum hydride (DIBAL-H), lithium borohydride ($LiBH_4$), sodium bis(2-methoxyethoxy)aluminum hydride (Red-Al), lithium aluminum hydride ($LiAlH_4$), potassium borohydride ($KBH_4$), Raney nickel, rhodium/hydrogen ($H_2$), palladium/hydrogen, platinum/hydrogen, rubidium/hydrogen, rubidium-silica/hydrogen, etc. Among them, sodium borohydride ($NaBH_4$) is particularly preferred.

In reaction c), the compound of formula (8) is treated with an acid such as trifluoroacetic acid to remove the hydroxy-protecting group of compound (8) and thereby produce the compound of formula (9), which is then treated with the compound of formula (18) in the presence of an acid, for example, methanol in the presence of hydrochloric acid to produce the compound of formula (10), which has a ribofuranose structure. The compound of formula (10) is then reacted with an acylchloride such as benzoyl chloride in the presence of a base to protect all the hydroxy groups of the compound of formula (10) with benzoyl groups, thereby producing the compound of formula (11). The compound of formula (11) is then treated with an acid such as acetic acid and anhydrous acetic acid in the presence of sulfuric acid to produce the compound of formula (12). The series of reaction steps for preparing the compound of formula (12) from the compound of formula (8) can preferably be practiced consecutively, without isolation of any intermediate.

In reaction d), the compound of formula (12) produced in reaction c) is treated with hydrogen chloride in a solvent such as dichloromethane, cyclohexane, chloroform, etc., and then treated with water in a solvent such as acetonitrile to produce the compound of formula (13). In this reaction, the reaction by-product 1-hydroxy-isomer must be removed by treating with ether such as dibutyl ether, diethyl ether, etc.

In reaction e), the compound of formula (13) is reacted with an agent for introducing a suitable reactive leaving group, for example, sulfuryl chloride and imidazole, to produce the compound of formula (14). This reaction can be carried out in the presence of a solvent such as dimethylformamide, dichloromethane, etc.

In reaction f), the compound of formula (14) produced in reaction e) is fluorinated in the presence of a solvent such as ethyl acetate, thereby substituting the reactive leaving group with fluorine to produce the compound of formula (15). In this reaction, the preferred fluorinating agent includes potassium hydrogen fluoride ($KHF_2$)/hydrofluoric acid/pyridine or hydrofluoric acid/amine such as triethylamine. The resulting compound of formula (15) is then halogenated, for example, with hydrobromic acid or hydrochloric acid, in the presence of acetic acid to produce the compound of formula (16). The compound of formula (16) is then reacted with a thymine base in the presence of hexamethyl-disilazane and ammonium sulfate to produce the compound of formula (17). This reaction can preferably be carried out in the presence of a solvent, for example, chloroform, dichloromethane, 1,2-dichloroethane, acetonitrile, etc.

In reaction g), the compound of formula (17) produced in reaction f) is treated with ammonia in the presence of a solvent to remove the benzoyl group, the hydroxy-protecting group, from the compound of formula (17), thereby producing the desired compound L-FMAU.

Although various aspects of the present invention are illustrated by the following examples, the present invention is not in any manner limited by these examples. Other reactants can be used as known to those of ordinary skill, which perform substantially the same function. In the examples, the number of the compound in parentheses corresponds to the number in the reaction scheme A.

EXAMPLE 1

Preparation of 1-O-benzyl-β-L-arabinoside (5)

Benzyl alcohol 1000 ml was saturated with hydrogen chloride for 40 minutes at 0° C., 200 g (1.33 mole) of L-arabinose was added and the resulting mixture was stirred at room temperature for 10 hours, during which a quantity of the compound (5) precipitated. To induce additional precipitation, 1.51 of ethyl acetate was slowly added while the mixture was stirred. The resulting solid product was filtered, washed with ethyl acetate and then dried in air to obtain 300 g (Yield: 94%) of the title compound (5) in the form of a white solid.

m.p.: 170–171° C. $^1$H NMR δ (ppm): 3.46 (q, 1H, J=2.87, 11.8), 3.63–3.73 (m, 4), 4.45 (d 1H, J=12.8), 4.76 (d, 1H, J=12.32), 7.29–7.38 (m, 5H)

EXAMPLE 2

Preparation of 1-O-benzyl-3,4-O-isopropylidene-β-L-riboside (8)

A mixture of 200 g (0.83 mole) of 1-O-benzyl-β-L-arabinoside (5), 240 ml (1.95 mole) of 2,2-dimethoxypropane and 4 g (0.02 mole) of p-TsOH H$_2$O in 2000 ml of acetone was stirred at room temperature for 2 hours. The reaction mixture thereby obtained was neutralized with triethylamine and evaporated under reduced pressure to obtain the compound (6) in the form of a yellowish syrup, which was used for the next reaction without further purification.

To a mixture of the compound (6) and 240 g (0.63 mole) of pyridinium dichromate in 2000 ml of dichloromethane was added 240 ml (2.54 mole) of acetic anhydride at 0° C. and the mixture thereby obtained was then refluxed until the starting material disappeared (ca. 4 hours). At this time, the system was vented. The solvent was removed under reduced pressure until the mixture occupied one-third of its initial volume and the residue was poured into 1500 ml of ethyl acetate with vigorous stirring accomplished using a mechanical stirrer. The mixture thus obtained was filtered through a celite pad and the filter cake was thoroughly washed with ethyl acetate. The blackish combined filtrate was filtered through a silica gel (2–20 micron) column (20 cm height, 10 cm diameter). The silica gel was washed with ethyl acetate until the compound (7) was no longer detected by TLC. The clear combined filtrate thereby obtained was evaporated to yield the compound (7) in the form of a syrup, which was coevaporated twice with toluene.

The purified syrup (7) thus obtained was dissolved in 2000 ml of methanol and cooled – to 20° C. NaBH$_4$ 40 g (1.06 mole) pellets were very slowly added to the resulting solution over 3 hours at −20° C. After completion of the reaction, the solution was neutralized with acetic acid, and evaporated under reduced pressure to obtain a white solid residue. The residue was partitioned between 1000 ml of ethyl acetate and 200 ml of water. The aqueous layer was extracted with 100 ml of ethyl acetate. The combined organic layer was washed with 200 ml of brine, dried over MgSO$_4$ and then evaporated to yield a white solid, which was recrystallized from 700 ml of hot hexane to yield 123 g (Yield: 53% from the compound (5)) of the compound (8) in the form of a white crystal.

m.p.: 79–80° C. $[α]^{25}_D$=+143° (c 0.7, ethanol) $^1$H NMR δ (ppm): 1.37 (s, 3H), 1.55 (s, 3H), 2.37 (d, 1H, J=6.45), 3.71–3.76 (m, 2), 3.86 (q, 1H, J=3.44 and 12.89), 4.27–4.30 (m, 1H), 4.49–4.52 (m, 1H), 4.56 (d, 1H, J=11.8), 4.83 (d, 1H, J=11.8), 4.86 (d, 1H, J=5.40), 7.26–7.36 (m, 5H)

EXAMPLE 3

Preparation of 1-O-acetyl-2,3,5-tri-O-benzoyl-β-L-ribofuranose (12)

201 g (0.717 mole) of the compound (8) dissolved in 11000 ml of 4% trifluoroacetic acid (CF$_3$COOH) was refluxed until the starting material (ca. 1 hour) and the intermediate (1-O-benzyl derivative) had disappeared (ca. 4–8 hours). The reaction mixture was cooled to room temperature and washed with dichloromethane (4×500 ml) to remove benzyl alcohol. The aqueous layer thereby obtained was evaporated in vacuo and coevaporated with toluene (2×200 ml) to yield the compound (9) in the form of a yellowish syrup, which was completely dried under high vacuum to remove a trace amount of water.

The compound (9) was dissolved in 2000 ml of methanol and 15.8 g (0.43 mole) of HCl (gas) was bubbled into the mixture at room temperature. The mixture thereby obtained was stirred at room temperature for 2 hours, neutralized with 183 ml of pyridine and concentrated in vacuo at 30–35° C. to give a yellowish syrup, which was in turn coevaporated with pyridine to yield the compound (10) in the form of a yellowish syrup. The compound (10) was dissolved in 800 ml of pyridine and 212 ml of benzoyl chloride was added dropwise to the mixture at 0° C. The mixture was stirred at room temperature for 8 hours. After the reaction had gone almost to completion, the mixture was heated at 45° C. for 1.5 hour. The mixture was cooled to room temperature and ice was added to remove the remaining benzoyl chloride. Pyridine was evaporated from the mixture at 35–40° C. until the mixture occupied half of its initial volume. The residue was dissolved in 1500 ml of ethyl acetate, which was washed in succession with 500 ml of cold water, 576 ml of cold 3N H$_2$SO$_4$, 500 ml of aqueous sodium bicarbonate (×2), and 500 ml of brine, in that order. The organic layer was dried over MgSO$_4$ and activated carbon, filtered through a silica gel (2–20μ) pad and evaporated to obtain the compound (11) in the form of a yellowish syrup.

To a mixture of the compound (11) dissolved in 144 ml (2.52 mole) of acetic acid and 334 ml (3.54 mole) of acetic anhydride, 48 ml (0.9 mole) of c-H$_2$SO$_4$ was slowly added dropwise at 0° C., during which crystallization occurred. The mixture was brought to room temperature and kept in a refrigerator overnight. The mixture was poured into 700 ml of an ice-water mixture, filtered and the filter cake was washed twice with cold water. The solid was dissolved in 2000 ml of ethyl acetate, which was washed in succession with 500 ml of water, 500 ml of saturated sodium bicarbonate and 500 ml of brine. The organic layer was dried over MgSO$_4$ and activated carbon and the resulting mixture was filtered through a silica gel (2–20 μ) pad. The solvent was removed and the residue was recrystallized from methanol to obtain 144.7 g (Yield: 40% from the compound (8)) of the compound (12) in the form of a white solid. m.p.: 124–125° C. $[α]^{25}_D$=−22.1° (c 1, pyridine)

$^1$H NMR(CDCl$_3$) δ (ppm): 8.90–7.32 (m, 15H, Ar—H), 6.43 (s, 1H, H-1), 5.91 (dd, 1H, H-3, J=4), 5.79 (d, 1H, H-2, J=8), 4.81–4.76 (m, 2H, H-4 and H-5), 4.54–4.49 (m, 1H, H-5), 2.00 (s, 3H, CH$_3$COO)

EXAMPLE 4

Preparation of 1,3,5-tri-O-benzoyl-α-L-ribofuranose (13)

HCl (gas) was bubbled for 1.5 hours into a solution of 50 g (99.16 mole) of the compound (12) dissolved in 460 ml of anhydrous dichloromethane and 7.5 ml of acetyl chloride at 0° C. The resulting solution was kept in a refrigerator for 12 hours and then evaporated in vacuo. The residue was coevaporated with toluene (3×150 ml) at 45° C. and redissolved in 105 ml of acetonitrile. To this solution, 13 ml of water was added dropwise at 0° C. A white solid began to precipitate from the mixture after 30 minutes, after which the mixture was kept in a refrigerator for 2 hours to induce additional precipitation. After filtration of the resulting solid, the filter cake was carefully washed with cold diethylether to remove the reaction by-product 1-hydroxy-isomer, which is indistinguishable by TLC from the compound (13). The white solid thereby obtained was dissolved in ethyl acetate. The solution was washed with saturated sodium bicarbonate to remove the remaining HCl, dried over $MgSO_4$ and filtered. The solvent was removed from the filtrate to obtain 29.2 g (Yield: 63.7%) of the compound (13) in the form of a white solid. m.p.: 137–139° C.

$[a]^{20}_D$=−82.01° (c 1.5, $CHCl_3$) $^1H$ NMR($CDCl_3$) δ (ppm): 7.31, 8.19(m, 15H, Ar—H), 6.69(d, J=4.6 Hz, 1H, H-1), 5.59 (dd, J=6.7, 1.8 Hz, 1H, H-3), 4.64, 4.80(m, 4H, H-2, H-4 and H-5), 2.30(br s, $D_2O$ exchangeable, OH)

EXAMPLE 5

Preparation of 1,3,5-tri-O-benzoyl-2-O-imidazolyl-sulfonyl-α-L-ribofuranose (14)

107.0 g (0.232 mole) of the compound (13) was dissolved in 1070 ml of dichloromethane and 214 ml of dimethylformamide, to which 62.5 g (37.2 ml, 0.463 mole) of sulfuryl chloride was added dropwise at a low temperature (−10 to −78° C.). The resulting solution was stirred at room temperature for 3 hours and then cooled in an ice-bath. The solution was stirred while 157.8 g (2.32 mole) of imidazole was added portionwise at the rate keeping the temperature of reaction mixture under 5° C. The resulting mixture was stirred at room temperature for 20 hours, after which 400 ml of ice-water was added. The aqueous layer was extracted three times with 100 ml of dichloromethane (3×100 ml). The combined organic solution was washed with 200 ml of brine and dried over $MgSO_4$. The solvent was removed under reduced pressure and dimethylformamide was removed under high vacuum. The syrupy residue was coevaporated with 100 ml of 2-propanol under reduced pressure to obtain a white solid product (14), which was used for the next reaction without further purification.

EXAMPLE 6

Preparation of 1-(3,5-di-O-benzoyl-2-fluoro-β-L-arabinofuranosyl)thymine (17)

A mixture of the imidazolate (14) obtained from Example 5, 224.1 g (1.39 mole) of triethylamine-3HF and 824 ml of ethyl acetate was heated at 80° C. for 3 hours, and then 70.3 g (92.5 ml, 0.696 mole) of triethylamine was slowly added thereto and the mixture thereby obtained was stirred for one additional hour at the same temperature, after which the mixture was cooled to room temperature. The resulting solution was poured into ice-water containing $NaHCO_3$ to neutralize it to pH 7. The aqueous layer was extracted three times with 100 ml of ethyl acetate (3×100 ml). The combined organic solution was washed with brine and dried over $Na_2SO_4$. The solvent was removed and the residue was redissolved in 300 ml of dichloromethane. The solvent was removed to obtain 101.0 g of crude 2-fluoro-sugar product (15), which was redissolved in 150 ml of dichloromethane. 195.9 ml (88.2 g, 1.09 mole) of hydrobromic acid/acetic acid(45% w/v) was added to the solution at 0° C. and then stirred at room temperature for 15 hours. The resulting solution was evaporated to dryness under reduced pressure to give a syrup, which was coevaporated with toluene (3×100 ml) to obtain the sugar bromide (16) in the form of a semisolid, which was then redissolved in 200 ml of chloroform for the condensation reaction described below.

A mixture of 55.44 g (0.44 mole) of thymine, 5 g of ammonium sulfate (($NH_4$)$_2SO_4$) and 212.5 g (278.9 ml, 1.32 mole) of hexamethyldisilazane in 1900 ml of chloroform was refluxed for 24 hours to give a nearly clear solution. A solution of sugar bromide (16) in chloroform was added and the resulting mixture was refluxed for additional 24 hours and then cooled to room temperature. 200 ml of water win the form of added to the reaction mixture, which was stirred at room temperature for 30 minutes and then filtered. The organic layer was separated, dried over $Na_2SO_4$, and filtered through a celite pad, which was then washed with ethyl acetate. The combined organic solution was evaporated to give a solid which was recrystallized from 100 ml of ethanol to obtain 78.0 g (Yield: 69.5% from the alcohol compound (13)) of 3,5-O-dibenzoyl L-FMAU (17) in the form of a crystal.

m.p.: 118–120° C. $[a]^{20}_D$=+22.40° (c 0.31, $CHCl_3$) UV (MeOH) $\lambda_{max}$ 264.0 nm $^1H$ NMR($CDCl_3$) δ (ppm): 8.55 (s, NH), 7.37, 8.12(m, Ar), 6.35(dd, $J_{F-H}$=22.4 Hz, H-1'), 5.64 (dd, $J_{FH}$=20.4 Hz, H-3'), 5.32(dd, $J_{F-H}$=500.2 Hz, H-2'), 4.82(m, H-5), 4.50(m, H-4'), 1.76(s, $CH_3$)

EXAMPLE 7

Preparation of 2'-fluoro-5-methyl-β-L-arabinofuranosyluridine (1)

$NH_3$ gas was bubbled for 2–3 hours into a suspension of 83.0 g (0.18 mole) of the compound (17) in 1000 ml of methanol to obtain a clear solution, which was then stirred at room temperature for an additional 48 hours. The solvent was removed under reduced pressure and the residue was triturated with diethyl ether. The resulting solid was collected by filtration, redissolved in 500 ml of methanol and twice decolorized with charcoal. Methanol was removed and the resulting solid was refluxed with 200 ml of acetonitrile for 2 hours. The resulting mixture was cooled in the refrigerator for 15 hours and then filtered to obtain 35.6 g (Yield: 77.35%) of a white solid. The mother liquor was concentrated to dryness and purified by silica gel column chromatography (1–10% methanol in chloroform) to obtain a white solid, which was refluxed with 20 ml of acetonitrile to obtain 4.98 g (Yield: 10.8%) of the second crop of the product. Total yield was raised to 88.2% (40.58 g).

m.p.: 185–187° C. $[a]^{20}_D$=−112.06° (c 0.23, methanol) UV ($H_2O$) $\lambda_{max}$ 265.0 (ϵ 9695)(pH 2), 265.5 (ϵ 9647) (pH 7), 265.5 nm (ϵ 7153)(pH 11) $^1H$ NMR (DMSO-d) δ (ppm): 11.45 (s, NH), 7.59 (s, H-6), 6.10 (dd, $J_{F-H}$=15.4 Hz, H-1'), 5.88 (d, 3'-OH), 5.12 (t, 5'-OH), 5.04 (dt, $J_{F-H}$=52.8 Hz, H-2'), 4.22 (dq, $J_{F-H}$=18.4 Hz, H-3'), 3.76 (m, H-4'), 3.63 (m, H-5'), 1.78 (s, $CH_3$)

This invention has been described with reference to its preferred embodiments. Variations and modifications of the invention will be obvious to those skilled in the art from the foregoing detailed description of the invention. It is intended that all of these variations and modifications be included within the scope of the appended claims.

What is claimed is:

1. A process for preparing 2'-fluoro-5-methyl-β-L-arabino-furanosyluridine (L-FMAU) of formula (1),

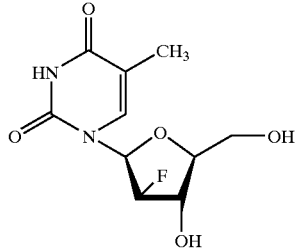
(1)

comprising:

a) reacting a L-arabinose of formula (4)

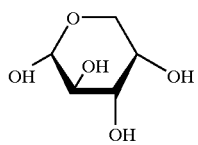
(4)

with a compound of formula (18)

R—OH        (18)

to obtain a compound of formula (5),

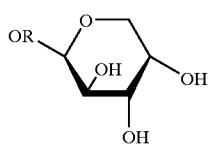
(5)

wherein R represents a benzyl, aryl or aralkyl group;

b) condensing the compound of formula (5) with a compound of formula (19)

H₃CO—C(R₁R₂)—OCH₃        (19)

to obtain the compound of formula (6);

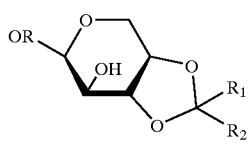
(6)

oxidizing the compound of formula (6) to obtain the compound of formula (7),

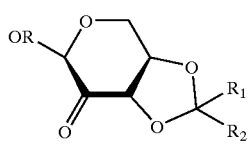
(7)

reducing the compound of formula (7) to obtain the compound of formula (8),

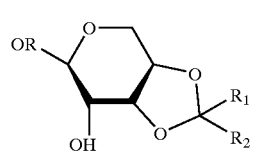
(8)

wherein $R_1$ and $R_2$ independently of one another represent hydrogen alkyl or aryl, and R represents a benzyl, aryl or aralkyl group;

c) treating the compound of formula (8) with an acid to obtain the compound of formula (9);

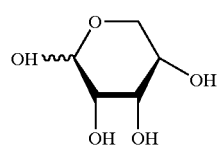
(9)

treating the compound of formula (9) with a compound of formula (18)

R—OH        (18)

wherein R represents a benzyl, aryl or aralkyl group;

in the presence of an acid to obtain the compound of formula (10);

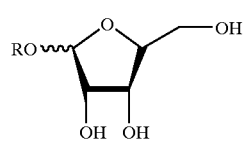
(10)

reacting and the compound of formula (10) with benzoyl chloride to obtain the compound of formula (11),

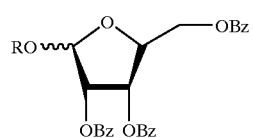
(11)

which is then reacted with acetic acid and acetic anhydride in the presence of acid to obtain the compound of formula (12);

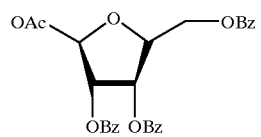
(12)

d) converting the compound of formula (12) into the compound of formula (13);

(13)

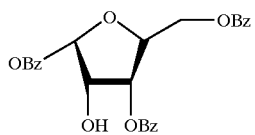

e) introducing a reactive leaving group into the compound of formula (13) to obtain the compound of formula (14), (14)

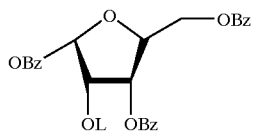

wherein L represents a reactive leaving group;

f) fluorinating the compound of formula (14) to obtain the compound of formula (15);

(15)

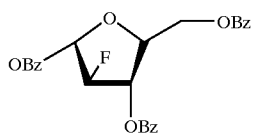

halogenating the compound of formula (15) to obtain the compound of formula (16);

(16)

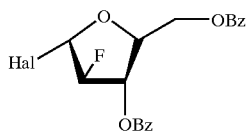

condensing the compound of formula (16) with thymine base to obtain the compound of formula (17), (17)

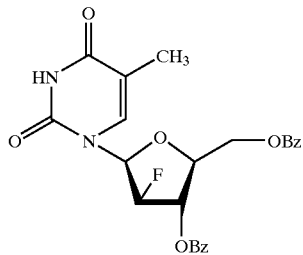

wherein Hal represents a halogen atom; and g) treating the compound of formula (17) with ammonia in methanol to produce the desired L-FMAU of formula (1).

2. The process as defined in claim 1, wherein the oxidation in reaction b) is carried out using aqueous chromic acid, sodium dichromate, pyridinium chlorochromate, pyridinium dichromate, potassium permanganate, lead tetraacetate/pyridine, oxygen over platinum/carbon catalyst, $RuO_4$, $RuO_4/NaIO_4$, dimethylsulfoxide/dicyclohexylcarbodiimide, a proton donor, silver carbonate, triphenyl bismuth carbonate, Oppenauer oxidation (aluminum alkoxides in acetone), chlorine dioxide, dimethylsulfoxide/oxalyl chloride, dimethylsulfoxide/sulfuryl chloride, dimethylsulfoxide/thionyl chloride, dimethylsulfoxide/toluene sulfonyl chloride, dimethylsulfoxide/trifluoroacetic anhydride or dimethylsulfoxide/acetic anhydride.

3. The process as defined in claim 1, wherein the reduction in reaction b) is carried out using sodium borohydride, diisobutylaluminum hydride, lithium borohydride, sodium bis(2-methoxyethoxy)aluminum hydride, lithium aluminum hydride, potassium borohydride, Raney nickel, rhodium/hydrogen, palladium/hydrogen, platinum/hydrogen, rubidium/hydrogen or rubidium-silica/hydrogen.

4. The process as defined in claim 1, wherein in the reaction d) the reaction by-product 1-hydroxy-isomer is removed using diethyl ether or dibutyl ether.

5. The process as defined in claim 1, wherein the reaction e) is carried out using imidazole and sulfuryl chloride.

6. The process as defined in claim 1, wherein the fluorination reaction in reaction f) is carried out using potassium hydrogen fluoride/hydrofluoric acid/pyridine or hydrofluoric acid/triethylamine.

7. The process as defined in claim 1, wherein the oxidation in reaction b) is carried out using aqueous chromic acid, sodium dichromate, pyridinium chlorochromate, or pyridinium dichromate.

8. The process as defined in claim 1, wherein the oxidation in reaction b) is carried out using pyridinium dichromate.

9. The process as defined in claim 1, wherein the reduction in reaction b) is carried out using sodium borohydride, lithium borohydride, or potassium borohydride.

10. The process as defined in claim 1, wherein the reduction in reaction b) is carried out using sodium borohydride.

11. The process as defined in claim 1, wherein the fluorination reaction in reaction f) is carried out using hydrofluoric acid/triethylamine.

12. The process as defined in claim 1, wherein the reaction of compound of formula 11 to formula 12 is in the presence of sulfuric acid.

* * * * *